United States Patent [19]
Prashad et al.

[11] Patent Number: 6,162,919
[45] Date of Patent: Dec. 19, 2000

[54] PROCESS FOR PREPARING THE D-THREO ISOMER OF METHYLPHENIDATE HYDROCHLORIDE

[75] Inventors: Mahavir Prashad, Montville; Bin Hu, North Plainfield, both of N.J.

[73] Assignee: Novartis AG, Basel, Switzerland

[21] Appl. No.: 09/204,460

[22] Filed: Dec. 3, 1998

[51] Int. Cl.$^7$ ................................................. C07D 211/32
[52] U.S. Cl. ............................................................. 546/233
[58] Field of Search ............................................. 546/233

[56] References Cited

U.S. PATENT DOCUMENTS

| | | | |
|---|---|---|---|
| 2,957,880 | 10/1960 | Rometsch | 546/233 |
| 5,733,756 | 3/1998 | Zeitlin et al. | 546/239 |

FOREIGN PATENT DOCUMENTS

| | | |
|---|---|---|
| WO 97/27176 | 7/1997 | WIPO . |
| WO 97/32851 | 9/1997 | WIPO . |
| WO 98/25902 | 6/1998 | WIPO . |

OTHER PUBLICATIONS

Journ. of Pharmacol. & Experimental Therapeutics, Patrick et al., vol. 241, pp. 152–158 (1987).

J.Med.Chem.,Thai, et al., vol. 41, pp. 591–601 (1998).

Tetrahedron: Asymmetry, vol. 9, pp. 2133–2136 (1998).

Journal of Chromatrography vol. 328, pp. 378–386 (1985).

*Primary Examiner*—John Kight
*Assistant Examiner*—Raymond Covington
*Attorney, Agent, or Firm*—Joseph J. Borovian

[57] ABSTRACT

A process for preparing the d-threo isomer of methylphenidate hydrochloride comprising converting d,l-threo methylphenidate hydrochloride to the free base form in a first step, resolving the free base prepared in the first step with (R)-(−)-1,1'-binaphthyl-2,2'-diyl hydrogen phosphate to obtain the phosphate salt enriched with the d-threo isomer of methylphenidate in a second step, basifying the phosphate salt to obtain the free base form of the d-threo isomer of methylphenidate in a third step, converting the free base to the hydrochloride salt form of the d-threo isomer of methylphenidate in high optical purity in a fourth step, and recrystallizing the hydrochloride salt form to obtain the desired d-threo isomer in a higher optical purity. An alternative embodiment relates to the preparation of the d-threo isomer of methylphenidate hydrochloride utilizing the hydrochloride salt form of the racemic mixture of threo-methylphenidate directly.

38 Claims, No Drawings

PROCESS FOR PREPARING THE D-THREO ISOMER OF METHYLPHENIDATE HYDROCHLORIDE

FIELD OF THE INVENTION

The present invention relates to the area of resolution processes and, more particularly, relates to an improved process for preparing the d-threo isomer of methylphenidate hydrochloride employing (R)-(−)-1,1'-binaphthyl-2,2'-diyl hydrogen phosphate as the resolving agent.

BACKGROUND OF THE INVENTION

Methylphenidate was first prepared as a mixture of the erythro and threo racemates. Subsequent studies of the two racemic mixtures revealed that the therapeutic activity resides in the threo diastereomer.

Racemic threo methylphenidate hydrochloride is a mild nervous system stimulant which is marketed for the treatment of children with Attention Deficit Hyperactivity Disorder (ADHD). Further studies of the threo diastereomer revealed that the preferred therapeutic activity resides in the d-threo (or 2R, 2'R enantiomer. More particularly, it has been found that the d-threo enantiomer is between five and thirty-eight times more active then the corresponding l-threo enantiomer. In addition, it has been shown that there are significant metabolic differences between the two enantiomers.

To date, several methods have been disclosed in the literature for preparing the d-threo enantiomer of methylphenidate. To wit, an enzymatic resolution is described in U.S. Pat. No. 5,733,756 and by M. Prashad, et al. in Tetrahedron:Asymmetry, Vol. 9, pgs. 2133–2136 (1998); a synthesis from enantiopure D-pipecolic acid is disclosed by D. L. Thai, et al. in J. Med. Chem., Vol. 41, pgs. 591–601 (1998); a HPLC resolution is described by H. K. Lim in Journal of Chromatography, Vol. 328, pgs. 378–386 (1985); and a recrystallization/crystallization method as well as an enzymatic resolution are disclosed in WO 98/25902. However, each of these methods exhibits one or more disadvantages and/or drawbacks which lend to their unattractiveness from a commercial standpoint.

In addition, U.S. Pat. No. 2,957,880 discloses a rather tedious sequence involving the resolution of the amide derivative of the corresponding erythro isomer, conversion to the threo isomer, followed by the hydrolysis of the amide to the corresponding acid, and esterification of the resulting acid with methanol. In the Journal of Pharmacology and Experimental Therapeutics, Vol. 241, pgs. 152–158 (1987), the d-threo enantiomer is prepared by resolving the racemic mixture of threo methylphenidate employing (R)-(−)-1,1'-binaphthyl-2,2'-diyl hydrogen phosphate. In WO 97/27176, the d-threo enantiomer is prepared by resolving racemic threo methylphenidate employing a di-aroyltartaric acid, preferably a ditoluoyltartaric acid, whereas in WO 97/32851, the d-threo enantiomer is prepared by resolving racemic threo methylphenidate employing (−)-menthoxyacetic acid. Although the latter three processes are believed to be more efficient than the resolution method disclosed in U.S. Pat. No. 2,957,880, they all exhibit drawbacks which make them unattractive from a commercial standpoint. To wit, the use of (R)-(−)-1,1'-binaphthyl-2,2'-diyl hydrogen phosphate as the resolving agent in the Journal of Pharmacology and Experimental Therapeutics article and the need for further recrystallizations to attain the desired purity renders the cost of the commercial process employing this method to be prohibitive. As to the latter two methods, they both involve the isolation of the free base form of the racemic mixture of threo methylphenidate prior to resolution. Accordingly, a need exists for a more practical and economic process for preparing the d-threo isomer of methylphenidate hydrochloride.

SUMMARY OF THE INVENTION

The present invention relates to an improved process for preparing the d-threo isomer of methylphenidate hydrochloride employing (R)-(−)-1,1'-binaphthyl-2,2'-diyl hydrogen phosphate as the resolving agent. The process of the present invention is believed to be more practical and economical since it utilizes far less of the resolving agent and allows the recovery of the resolving agent. Another advantage of the present invention is provided by an alternative embodiment which enables the preparation of the d-threo isomer of methylphenidate hydrochloride utilizing the hydrochloride salt form of the racemic mixture of threo-methylphenidate directly (i.e., it avoids the isolation of, or conversion to, the free base form of the racemic mixture of threo methylphenidate prior to resolution), which embodiment is described in detail hereinafter. In any event, the process of the present invention involves the conversion of d,l-threo-methylphenidate hydrochloride to the free base form in a first step, the resolution of said free base with (R)-(−)-1,1'-binaphthyl-2,2'-diyl hydrogen phosphate to yield the desired phosphate salt enriched with the d-threo (2R,2'R) isomer of methylphenidate in a second step, the basification of said salt to obtain the free base form of the desired d-threo isomer in a third step, the conversion of the free base into the hydrochloride salt form of the desired d-threo isomer in high optical purity in a fourth step, and the recrystallization of said salt in a last step to obtain the desired d-threo isomer in a higher optical purity.

DETAILED DESCRIPTION OF THE INVENTION

The present invention relates to an improved process for preparing the d-threo isomer of methylphenidate hydrochloride by a five-step process as depicted below:

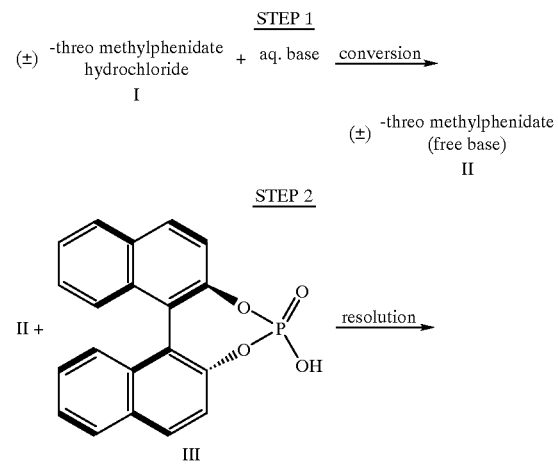

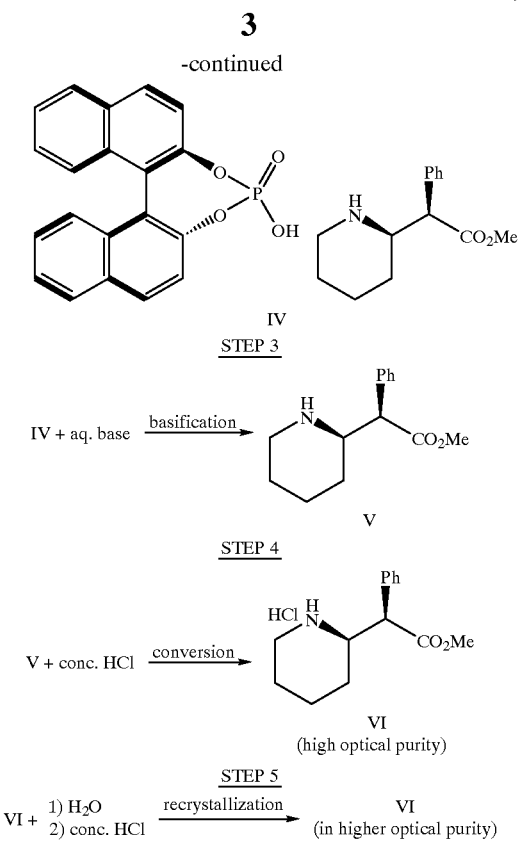

IV
STEP 3

IV + aq. base —basification→ V

STEP 4

V + conc. HCl —conversion→ VI (high optical purity)

STEP 5

VI + 1) H₂O  2) conc. HCl —recrystallization→ VI (in higher optical purity)

With respect to the individual steps, Step 1 involves the conversion of the racemic mixture of threo methylphenidate hydrochloride to the free base form. More particularly, the conversion involves the addition of an aqueous mixture of an alkali metal hydroxide, preferably sodium hydroxide, and sodium chloride to the hydrochloride in the presence of an inert, organic solvent, preferably isopropyl acetate. The conversion to the free base form is carried out at a temperature of from 15° to 25° C. for a period of between 30 and 60 minutes.

The second step involves the resolution of the free base obtained in Step 1 to the desired phosphate salt enriched with the d-threo isomer of methylphenidate. More particularly, the resolution involves the reaction of the free base obtained in Step 1 with 0.5 equivalents of (R)-(−)-1, 1'-binaphthyl-2,2'-diyl hydrogen phosphate in a mixture of isopropyl acetate and methanol in a v/v ratio of 95:5 to 80:20, more preferably 85:15, to obtain the desired phosphate salt of formula IV. The resolution is carried out at an initial temperature of from 60° to 70° C. for a period of between 30 and 60 minutes, then at a temperature of from 15° to 30° C. for a period of between 90 minutes and 4 hours, and finally at a temperature of from 0° to 10° C. for a period of between 90 minutes and 3 hours.

The third step involves the basification of the phosphate salt obtained in Step 2, i.e. the compound of formula IV, with an alkali metal hydroxide solution, preferably a sodium hydroxide solution, in the presence of an inert, organic solvent, preferably isopropyl acetate, to obtain the free base form of the desired d-threo isomer, i.e., the compound of formula V. The basification is carried out at a temperature of from 15° to 30° C. for a period of between 30 and 60 minutes.

The fourth step concerns the conversion of the free base obtained in Step 3, i.e. the compound of formula V, into the hydrochloride salt form of the desired d-threo isomer in high optical purity. The conversion is carried out by adding concentrated hydrochloric acid to the free base (which has been pre-cooled to between 0° and 5° C.), and then allowing the mixture to react at a temperature of from 5° to 25° C. for a period of between 30 minutes and 2 hours to obtain the compound of formula VI.

The last step involves the recrystallization of the hydrochloride salt obtained in Step 4, i.e., the compound of formula VI, by the addition of concentrated hydrochloric acid to an aqueous solution of the hydrochloride salt. The resultant mixture is then allowed to react at a temperature of from 0° to 10° C. for a period of between 30 and 60 minutes to obtain the hydrochloride salt in a higher optical purity.

Although not essential, it is preferred that the resolution in Step 2 be carried out in the presence of a crystallization-inducing amount of pure (R)-(−)-1,1'-binaphthyl-2,2'-diyl hydrogen phosphate salt seeds enriched with the d-threo isomer of methylphenidate, which seeds may be obtained by adding a solution of the free base form of the desired d-threo isomer of methylphenidate in ethyl acetate to an equimolar solution of (R)-(−)-1,1'-binaphthyl-2,2'-diyl hydrogen phosphate in ethyl acetate. The mixture is then allowed to react at a temperature of from 0° to 10° C. for a period of between 30 and 60 minutes.

Alternatively, the resolution in Step 2 may be carried out by reacting the free base obtained in Step 1 with 0.5 equivalents of (R)-(−)-1,1'-binaphthyl-2,2'-diyl hydrogen phosphate in a mixture of acetone and methanol in a v/v ratio of 98:2 to 95:5, more preferably 98:2, to obtain the desired phosphate salt of formula IV. The resolution is carried out at an initial temperature of from 60° to 70° C. for a period of between 30 and 60 minutes, and then at a temperature of from 15° to 30° C. for a period of between 12 and 24 hours.

As indicated above, an alternative embodiment of the present invention provides another advantage in that it enables the preparation of the d-threo isomer of methylphenidate hydrochloride utilizing the hydrochloride salt form of the racemic mixture of threo-methylphenidate directly. More particularly, the alternative embodiment comprises a four-step process as depicted below:

STEP 1A

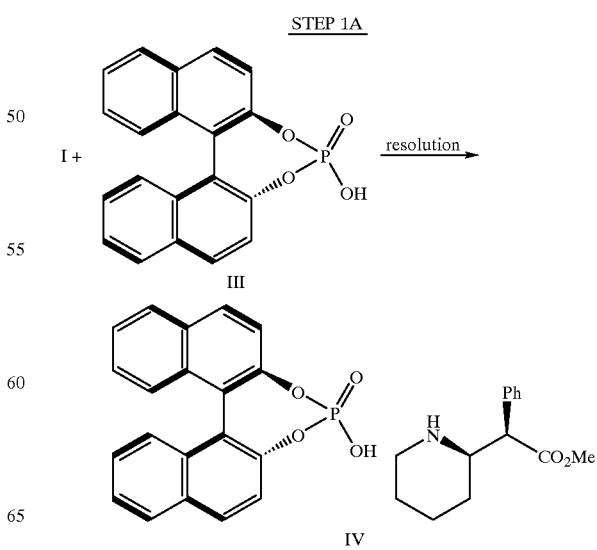

-continued

STEP 2A

IV + aq. base —basification→

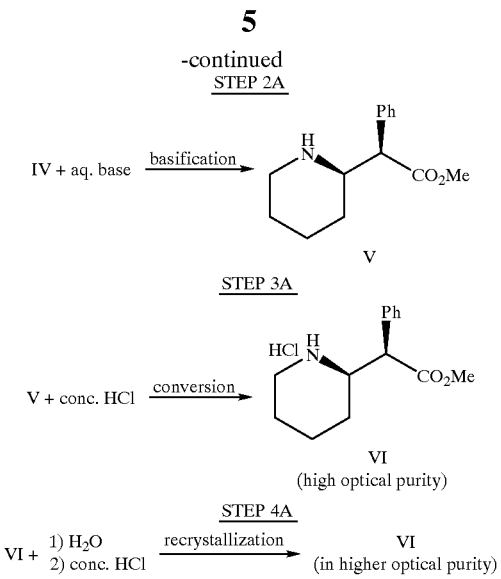

STEP 3A

V + conc. HCl —conversion→

VI
(high optical purity)

STEP 4A

VI + 1) H₂O  —recrystallization→  VI
    2) conc. HCl                  (in higher optical purity)

As regards the individual steps, Step 1A involves the resolution of the racemic mixture of threo methylphenidate hydrochloride to the desired phosphate salt enriched with the d-threo isomer of methylphenidate. More particularly, the resolution involves the reaction of the hydrochloride with 0.5 equivalents of (R)-(−)-1,1'-binaphthyl-2,2'-diyl hydrogen phosphate in the presence of an aqueous solvent, e.g., a mixture of a lower alkanol and water, and a base to obtain the desired phosphate salt of formula IV. The aqueous solvent is preferably a mixture of methanol or ethanol in water in a ratio of between 1.5 and 1.8:1, more preferably a mixture of methanol and water in a ratio of about 1.6:1. Any base may be employed in the reaction as long as the salt of the base with the resolving agent, viz., (R)-(−)-1,1'-binaphthyl-2,2'-diyl hydrogen phosphate, remains dissolved in the aqueous solvent. Suitable bases that may be employed are 4-methylmorpholine, an alkali metal hydroxide or a tri-lower alkyl amine, preferably 4-methylmorpholine, sodium hydroxide or triethylamine, more preferably 4-methylmorpholine. The reaction is conducted at an initial temperature of from 40° to 50° C. for a period of between 15 and 45 minutes, and then at a temperature of from 15° to 30° for a period of between 1 and 4 hours.

With regard to Steps 2A through 4A, they are carried out in essentially an analogous manner to Steps 3 through 5 described above.

As was the case in Step 2 of the five-step method described above, although not essential, it is preferred that the resolution in Step 1A be carried out in the presence of a crystallization-inducing amount of pure (R)-(−)-1,1'-binaphthyl-2,2'-diyl hydrogen phosphate salt seeds enriched with the d-threo isomer of methylphenidate.

As alluded to above, racemic threo methylphenidate hydrochloride is known and commercially available, as is the resolving agent employed in Steps 2 and 1A, viz., (R)-(−)-1,1'-binaphthyl-2,2'-diyl hydrogen phosphate. In the latter connection, another advantage of the process of the invention is that the resolving agent is recyclable. Thus, the (R)-(−)-1,1'-binaphthyl-2,2'-diyl hydrogen phosphate may be recovered by: 1) combining the sodium salt thereof obtained by basifying the filtrate from Step 2, collecting the solid by filtration, and extracting the solid with isopropyl acetate, with the sodium salt and aqueous layer obtained in Step 3; 2) allowing the mixture to react at reflux temperature for between 30 and 45 minutes; and 3) treating the mixture with concentrated hydrochloric acid, initially at the reflux temperature for between 30 and 60 minutes, and then at a temperature of between 15° and 30° C. for a period of between 3 and 5 hours. The recovered (R)-(−)-1,1'-binaphthyl-2,2'-diyl hydrogen phosphate is of comparable purity to that of the commercially available material. A resolution of the free base form of racemic threo methylphenidate with the recovered material yielded the desired phosphate salt enriched with the d-threo isomer of methylphenidate.

As is fairly evident, the l-threo isomer of methylphenidate hydrochloride in high purity may be prepared by the process of this invention by utilizing (S)-(+)-1,1'-binaphthyl-2,2'-diyl hydrogen phosphate as the resolving agent in Step 2 or Step 1A of the alternative embodiment.

Although the desired phosphate salt obtained in Step 2 or in Step 1A of the alternative embodiment may, if desired, be purified by conventional techniques such as recrystallization, the crude phosphate salt is advantageously employed in Step 3 or in Step 2A of the alternative embodiment without purification.

The following examples are for purposes of illustration only and are not intended to limit in any way the scope of the instant invention.

EXAMPLE 1

Preparation of d-threo Isomer of Methylphenidate Hydrochloride (in the Presence of Pure (R)-(−)-1,1'-binaphthyl-2,2'-diyl Hydrogen Phosphate Salt Seeds)

a) Preparation of the Free Base Form of the Racemic Mixture of threo-methylphenidate To a 1-L, 4-necked, round-bottomed flask, equipped with a mechanical stirrer, digital thermometer, nitrogen inlet-outlet, heating-cooling bath and addition funnel, is added 72.85 g (0.27 mol) of d,l-threo methylphenidate hydrochloride and 450 ml of isopropyl acetate. The mixture is then stirred at a temperature between 20° and 25° C. under nitrogen, and to the mixture is then added a pre-cooled (20° to 25° C.) solution of 18.0 g of sodium hydroxide and 72.0 g of sodium chloride in 315 ml of water over a period of 5 minutes while the temperature is maintained at between 20° and 25° C. The resulting suspension is then stirred until all of the solid dissolves (~30 minutes), and the organic layer is separated and line-filtered to obtain the desired free base as a solution.

b) Preparation of (R)-(−)-1,1'-binaphthyl-2,2'-diyl Hydrogen Phosphate Salt Enriched With the d-threo Isomer of Methylphenidate To a 3-L, 4-necked, round-bottomed flask, equipped with a mechanical stirrer, digital thermometer, nitrogen inlet-outlet, heating mantle, condenser and addition funnel, is added 47.02 g (0.135 mol) of (R)-(−)-1,1'-binaphthyl-2,2'-diyl hydrogen phosphate, 202.5 ml of methanol and 652.5 ml of isopropyl acetate. The resulting suspension is then stirred under nitrogen, and heated to 65° C., over a period of 15 minutes, to achieve gentle refluxing. To the heated suspension is added ~500 ml of the free base obtained in a) above, while the temperature is maintained at between 60° and 65° C., which results in a clear solution. The addition funnel is then washed with 45 ml of isopropyl acetate and after the washing is added to the clear solution, 50 mg of (R)-(−)-1,1'-binaphthyl-2,2'-diyl hydrogen phosphate salt seeds enriched with the d-threo isomer of methylphenidate (obtained essentially as described earlier in the specification) is added. The reaction mixture is then cooled to between 20° and 25° C. over a period of 2 hours, and then stirred for an additional 2 hours while the temperature is maintained at between 20° and 25° C. The heterogeneous mixture is then cooled to between 0° and 5° C. over a period of 15 minutes, and then stirred for an additional 2 hours while the temperature is maintained at between 0° and 5° C. The mixture is then filtered over a polypropylene filter paper in a Buchner funnel with suction, and the crude solid is washed with 150 ml of a pre-cooled (0° to 2° C.) mixture of isopropyl acetate and methanol (in a 85:15 v/v ratio) in 2 equal portions of 75 ml each (the filtrate is reserved for use in the recovery of the resolving agent). The solid is then dried at a temperature between 50° and 55° C. (100 mmHg) to obtain the desired phosphate salt as a white solid (2R,2'R:2S,2'S ratio is 99.2:0.8).

c) Preparation of the Free Base Form of d-threo Methylphenidate

To a 3-L, 4-necked, round-bottomed flask, equipped with a mechanical stirrer, digital thermometer, nitrogen inlet-outlet and addition funnel is added 56.85 g of the phosphate salt obtained in b) above, 853 ml of isopropyl acetate and 942 ml of water. The mixture is then stirred at a temperature of between 20° and 25° C. under nitrogen, and a solution of 23.46 g of sodium hydroxide in 195 ml of water is added, over a period of between 5 and 10 minutes, while the temperature is maintained between 20° and 25° C. All the solid is dissolved and another solid precipitates out immediately. The 3-phase mixture is then stirred for 30 minutes and then filtered over a polypropylene filter paper in a Buchner funnel with suction. The biphasic filtrate is transferred to a separatory funnel and the solid (the sodium salt of (R)-(−)-1,1'-binaphthyl-2,2'-diyl hydrogen phosphate) is washed with 855 ml of isopropyl acetate in three equal portions of 285 ml each and reserved for use in the recovery of the resolving agent. The organic layer is then separated from the biphasic filtrate and the aqueous layer is extracted with 855 ml of the isopropyl acetate filtrate and reserved for use in the recovery of the resolving agent. The organic layers are then combined, washed with 50 ml of water and line-filtered to obtain the desired free base as a solution.

d) Preparation of the Hydrochloride Salt Form of d-threo Methylphenidate in a High Optical Purity To a 3-L, 4-necked, round-bottomed flask, equipped with a mechanical stirrer, digital thermometer, nitrogen inlet-outlet, cooling bath and addition funnel, is added ~1650 ml of the solution of free base obtained in c) above which is then cooled to a temperature between 0° and 2° C. To the cooled solution is then added, over a period of 10 minutes, 14.45 g of concentrated hydrochloric acid (37%), while the temperature is maintained at less than 10° C. The reaction mixture is then warmed to a temperature between 20° and 22° C., over a period of 45 minutes, filtered and the resultant solid is washed with 50 ml of isopropyl acetate, in 2 equal portions of 25 ml each, and dried at a temperature between 55° and 58° C. (100 mmHg) to obtain the desired hydrochloride salt as a white solid (2R,2'R:2S,2'S ratio is 99.2:0.8).

e) Preparation of the Title Compound in a Higher Optical Purity

To a 250 ml, 4-necked, round-bottomed flask, equipped with a mechanical stirrer, digital thermometer, nitrogen inlet-outlet, heating mantle, condenser and addition funnel, is added 29 g of deionized water which is then heated to a temperature of between 74° and 75° C. To the heated water is then added 24.62 g of the hydrochloride salt obtained in d) above, and the mixture is heated to a temperature between 80° and 82° C. The resultant clear solution is then cooled to a temperature of between 20° and 22° C., over a period of 45 minutes. To the resultant heterogeneous mixture is then added 9.0 g of concentrated hydrochloric acid (37%), over a period of 10 minutes, while the temperature is maintained at less than 25° C. The mixture is then cooled to a temperature between 0° and 5° C., over a period of 15 minutes, and then stirred at this temperature for an additional 30 minutes. The mixture is then filtered and the resultant solid is washed with 8 ml of pre-cooled water (between 0° and 5° C.) in 2 equal portions of 4 ml each, and dried at a temperature between 50° and 55° C. (100 mmHg) to obtain the desired title compound as a white crystalline solid (2R,2'R:2S,2'S ratio is 100:0, i.e., the 2S,2'S enantiomer was undetectable).

EXAMPLE 2

Preparation of the d-threo Isomer of Methylphenidate Hydrochloride (in the Absence of Pure (R)-(−)-1,1'-binaphthyl-2,2'-diyl Hydrogen Phosphate Salt Seeds)

a) Preparation of (R)-(−)-1,1'-binaphthyl-2,2'-diyl Hydrogen Phosphate Salt Enriched With the d-threo Isomer of Methylphenidate Following essentially procedure b) of Example 1, with the exception that the pure (R)-(−)-1,1'-binaphthyl-2,2'-diyl hydrogen phosphate salt seeds are not added, the desired phosphate salt is obtained as a white solid.

b) Preparation of the Title Compound

Following essentially procedures c), d) and e) of Example 1, with the exception that an approximately equivalent amount of the phosphate salt obtained in a) above is used as the starting material in procedure c) instead of the phosphate salt obtained in procedure b) of Example 1, the title compound is obtained as a white crystalline solid.

EXAMPLE 3

Preparation of l-threo Isomer of Methylphenidate Hydrochloride a) Preparation of (S)-(+)-1,1'-binaphthyl-2,2'-diyl Hydrogen Phosphate Salt Enriched With the l-threo Isomer of Methylphenidate Following essentially procedure b) of Example 1, with the exception that an approximately equivalent amount of (S)-(+)-1,1'-binaphthyl-2,2'-diyl hydrogen phosphate is used instead of (R)-(−)-1,1'-binaphthyl-2,2'-diyl hydrogen phosphate, and with the further exception that the pure (R)-(−)-1,1'-binaphthyl-2,2'-diyl hydrogen phosphate salt seeds are not added, the desired phosphate salt is obtained as a white solid.

b) Preparation of the Title Compound

Following essentially procedures c), d) and e) of Example 1, with the exception that an approximately equivalent amount of the phosphate salt obtained in a) above is used as the starting material in procedure c) instead of the phosphate salt obtained in procedure b) of Example 1, the title compound is obtained as a white crystalline solid.

EXAMPLE 4

Procedure for the Recovery of the (R)-(−)-1,1'-binaphthyl-2,2'-diyl Hydrogen Phosphate Resolving Agent a) Preparation of the Sodium Salt of (R)-(−)-1,1'-binaphthyl-2,2'-diyl Hydrogen Phosphate To a 3-L, 4-necked, round-bottomed flask, equipped with a mechanical stirrer, digital thermometer, nitrogen inlet-outlet, cooling bath and addition funnel is added ~1320 ml of the filtrate that was reserved in procedure b) of Example 1. The mixture is stirred at a temperature of between 20° and 25° C. under nitrogen, and a solution of 10.80 g of sodium hydroxide and 126.0 g of sodium chloride in 540 ml of water is added, over a period of 20 minutes, while the temperature is maintained at less than 25° C. A solid precipitates out immediately and the heterogeneous mixture is stirred for 3 hours while the temperature is maintained at between 20° and 25° C. The mixture is then filtered over a polypropylene filter paper in a Buchner funnel with suction, and the solid is washed with 30 ml of isopropyl acetate, and dried at 50°–55° C. (100 mmHg) to obtain the desired sodium salt as a white solid.

b) Recovery of Resolving Agent

To a 3-L, 4-necked, round-bottomed flask, equipped with a mechanical stirrer, digital thermometer, nitrogen inlet-outlet, heating mantle and addition funnel is added 38.88 g of the sodium salt that was reserved from procedure c) in Example 1, 6.25 g of the sodium salt obtained in a) above, and ~1200 ml of the aqueous layer that was reserved from procedure c) in Example 1 at a temperature between 20° and 25° C. The heterogeneous mixture is then heated, with stirring over a period of 30 minutes, to reflux temperature (between 90° and 95° C.) which results in a clear solution. To the clear solution is added 117.81 g of concentrated hydrochloric acid (37%) over a period of 10 minutes, while the reflux temperature is maintained. The resultant heterogeneous mixture is then refluxed for an additional 30 minutes, cooled to room temperature (between 20° and 22° C.) over a period of 1 hour, and stirred at this temperature for an additional 3 hours. The mixture is then filtered over a polypropylene filter paper in a Buchner funnel with suction, and the solid is washed with 25 ml of 6N hydrochloric acid and then 25 ml of water, and dried at 50°–55° C. (100 mmHg) to obtain the desired resolving agent as a white solid in a purity equivalent to the commercial material.

EXAMPLE 5

Alternate Preparation of the d-threo Isomer of Methylphenidate Hydrochloride (in the Absence of Pure (R)-(−)-1,1'-binaphthyl-2,2'-diyl Hydrogen Phosphate Salt Seeds and Employing a Different Solvent Mixture in the Resolving Step)

a) Preparation of (R)-(−)-1,1'-binaphthyl-2,2'-diyl Hydrogen Phosphate Salt Enriched With the d-threo Isomer of Methylphenidate To a 50 ml, 3-necked, round-bottomed flask, equipped with a magnetic stirrer, digital thermometer, nitrogen inlet-outlet, heating mantle and condenser is added 0.70 g of the free base form of d,l-threo methylphenidate, 0.52 g of (R)-(−)-1,1'-binaphthyl-2,2'-diyl hydrogen phosphate and 15 ml of a mixture of acetone and methanol (in a 98:2 v/v ratio). The resulting suspension is then stirred under nitrogen, and heated to 65° C., over a period of 15 minutes, to achieve gentle refluxing. All the solid is dissolved and another solid precipitates out immediately. The heterogeneous reaction mixture is then stirred for an additional 10 minutes, while maintaining the reflux temperature. The reaction mixture is then cooled to room temperature (between 20° and 25° C.) over a period of 1 hour, and then stirred at this temperature overnight (~16 hours). The mixture is then filtered over a polypropylene filter paper in a Buchner funnel with suction, and the solid is washed with 2 ml of a mixture of acetone and methanol (in a 98:2 v/v ratio) in 2 equal portions of 1 ml each. The solid is then dried at 50°–55° C. (100 mmHg) to obtain the desired phosphate salt as a white solid (2R,2'R:2S, 2'S ratio is 99.9:0.1).

b) Preparation of the Title Compound

Following essentially procedures c), d) and e) of Example 1, with the exception that an approximately equivalent amount of the phosphate salt obtained in a) above is used as the starting material in procedure c) instead of the phosphate salt obtained in procedure b) of Example 1, the title compound is obtained as a white crystalline solid (2R,2'R:2S,2'S ratio is 100:0).

EXAMPLE 6

Preparation of d-threo Isomer of Methylphenidate Hydrochloride Directly From the Racemic Mixture of Threo-Methylphenidate Hydrochloride (in the Presence of Pure (R)-(−)-1,1'-binaphthyl-2,2'-diyl Hydrogen Phosphate Salt Seeds)

a) Preparation of (R)-(−)-1,1'-binaphthyl-2,2'-diyl Hydrogen Phosphate Salt Enriched With the d-threo Isomer of Methylphenidate To a 50-ml, 3-necked, round-bottomed flask, equipped with a magnetic stirrer, digital thermometer, nitrogen inlet-outlet, heating mantle and condenser is added 0.81 g (0.003 mol) of d,l-threo methylphenidate hydrochloride, 0.52 g (0.0015 mol) of (R)-(−)-1,1'-binaphthyl-2,2'-diyl hydrogen phosphate, 0.30 g of 4-methylmorpholine and 9.6 ml of methanol, and the suspension is stirred under nitrogen which results in a clear solution. The reaction mixture is then heated to a temperature between 40° and 50° C., and 6 ml of water are added. To the reaction mixture is then added 2 mg of (R)-(−)-1,1'-binaphthyl-2,2'-diyl hydrogen phosphate salt seeds enriched with the d-threo isomer of methylphenidate, and the resultant mixture is cooled to between 20° and 25° C. over a period of 1 hour. The mixture is then stirred for an additional 3 hours, while the temperature is maintained at between 20° and 25° C. The mixture is then filtered over a polypropylene filter paper in a Buchner funnel with suction, and the solid is washed with 2 ml of a mixture of methanol and water (in a 1.6:1 v/v ratio) in 2 equal portions of 1 ml each. The solid is then dried at 50°–55° C. (100 mmHg) to obtain the desired phosphate salt as a white solid (2R,2'R:2S,2'S ratio is 99.1:0.9).

b) Preparation of the Title Compound

Following essentially procedures c), d) and e) of Example 1, with the exception that an approximately equivalent amount of the phosphate salt obtained in a) above is used as the starting material in procedure c) instead of the phosphate salt obtained in procedure b) of Example 1, the title compound is obtained as a white crystalline solid (2R,2'R:2S,2'S ratio is 100:0).

What is claimed is:

1. A process for preparing the d-threo isomer of methylphenidate comprising the steps of:

1) converting d,l-threo methylphenidate hydrochloride to the free base form;

2) resolving the free base prepared in Step 1 with 0.5 equivalents of (R)-(−)-1,1'-binaphthyl-2,2'-diyl hydrogen phosphate to obtain the phosphate salt enriched with the d-threo isomer of methylphenidate;

3) basifying the phosphate salt prepared in Step 2 to obtain the free base form of d-threo methylphenidate;

4) converting the free base prepared in Step 3 into the hydrochloride salt form of d-threo methylphenidate in high optical purity; and 5) recrystallizing the salt prepared in Step 4 to obtain the desired d-threo isomer in a higher optical purity.

2. A process according to claim 1 wherein the conversion in the first step is carried out by adding an aqueous mixture of an alkali metal hydroxide and sodium chloride to the hydrochloride in the presence of an inert, organic solvent.

3. A process according to claim 2 wherein the alkali metal hydroxide is sodium hydroxide.

4. A process according to claim 2 wherein the solvent is isopropyl acetate.

5. A process according to claim 1 wherein the resolution in the second step is carried out in the presence of a mixture of isopropyl acetate and methanol in a v/v ratio of 95:5 to 80:20.

6. A process according to claim 1 wherein the second step is carried out at an initial temperature of from 60° to 70° C. for a period of between 30 and 60 minutes, then at a temperature of from 15° to 30° C. for a period of between 90 minutes and 4 hours and finally at a temperature of from 0° to 10° C. for a period of between 90 minutes and 3 hours.

7. A process according to claim 1 wherein the second step is carried out in the presence of a crystallization-inducing amount of pure (R)-(−)-1,1'-binaphthyl-2,2'-diyl hydrogen phosphate salt seeds enriched with the d-threo isomer of methylphenidate.

8. A process according to claim 1 wherein the third step is carried out with an alkali metal hydroxide solution.

9. A process according to claim 8 wherein the third step is carried out with a sodium hydroxide solution.

10. A process according to claim 1 wherein the third step is carried out in the presence of an inert, organic solvent.

11. A process according to claim 10 wherein the solvent is isopropyl acetate.

12. A process according to claim 1 wherein the third step is carried out at a temperature of from 15° to 30° C. for a period of between 30 and 60 minutes.

13. A process according to claim 1 wherein the fourth step is carried out by adding concentrated hydrochloric acid to the free base obtained in the second step which is pre-cooled to a temperature between 0° and 5° C.

14. A process according to claim 13 wherein the fourth step is carried out at a temperature of from 5° to 30° C. for a period of between 30 minutes and 2 hours.

15. A process according to claim 1 wherein the fifth step is carried out by adding concentrated hydrochloric acid to an aqueous solution of the hydrochloride salt obtained in the third step.

16. A process according to claim 15 wherein the fifth step is carried out at a temperature of from 0° to 10° C. for a period of between 30 and 60 minutes.

17. A process according to claim 1 wherein the resolution in the second step is carried out in the presence of a mixture of acetone and methanol in a v/v ratio of 98:2 to 95:5.

18. A process according to claim 17 which is carried out at an initial temperature of from 60° to 70° C. for a period of between 30 and 60 minutes, and then at a temperature of from 15° to 30° C. for a period of between 12 and 24 hours.

19. A process for preparing the d-threo isomer of methylphenidate hydrochloride directly from the racemic mixture of threo methylphenidate hydrochloride comprising the steps of:

1) resolving d,l-threo methylphenidate hydrochloride with 0.5 equivalents of (R)-(−)-1,1'-binaphthyl-2,2'-diyl hydrogen phosphate to obtain the phosphate salt enriched with the d-threo isomer of methylphenidate;

2) basifying the phosphate salt prepared in Step 1 to obtain the free base form of d-threo methylphenidate;

3) converting the free base prepared in Step 2 into the hydrochloride salt form of d-threo methylphenidate in high optical purity; and 4) recrystallizing the salt prepared in Step 3 to obtain the desired d-threo isomer in a higher optical purity.

20. A process according to claim 19 wherein the first step is carried out in the presence of an aqueous solvent.

21. A process according to claim 20 wherein the aqueous solvent is a mixture of a lower alkanol and water.

22. A process according to claim 21 wherein the aqueous solvent is a mixture of methanol or ethanol and water in a ratio of between 1.5 and 1.8.

23. A process according to claim 22 wherein the aqueous solvent is a mixture of methanol and water in a ratio of about 1.6.

24. A process according to claim 19 wherein the first step is carried out in the presence of a base.

25. A process according to claim 24 wherein the base is selected from 4-methylmorpholine, an alkali metal hydroxide and a tri-lower alkyl amine.

26. A process according to claim 25 wherein the base is selected from 4-methylmorpholine, sodium hydroxide and triethylamine.

27. A process according to claim 26 wherein the base is 4-methylmorpholine.

28. A process according to claim 19 wherein the first step is carried out at an initial temperature of from 40° to 50° C. for a period of between 15 and 45 minutes, and then at a temperature of from 15° to 30° C. for a period of between 1 and 4 hours.

29. A process according to claim 19 wherein the first step is carried out in the presence of a crystallization-inducing amount of pure (R)-(−)-1,1'-binaphthyl-2,2'-diyl hydrogen phosphate salt seeds enriched with the d-threo isomer of methylphenidate.

30. A process according to claim 19 wherein the second step is carried out with an alkali metal hydroxide solution.

31. A process according to claim 30 wherein the second step is carried out with a sodium hydroxide solution.

32. A process according to claim 19 wherein the second step is carried out in the presence of an inert, organic solvent.

33. A process according to claim 32 wherein the solvent is isopropyl acetate.

34. A process according to claim 19 wherein the second step is carried out at a temperature of from 15° to 30° C. for a period of between 30 and 60 minutes.

35. A process according to claim 19 wherein the third step is carried out by adding concentrated hydrochloric acid to the free base obtained in the second step which is pre-cooled to a temperature between 0° and 5° C.

36. A process according to claim 35 wherein the third step is carried out at a temperature of from 5° to 30° C. for a period of between 30 minutes and 2 hours.

37. A process according to claim 19 wherein the fourth step is carried out by adding concentrated hydrochloric acid to an aqueous solution of the hydrochloride salt obtained in the third step.

38. A process according to claim 37 wherein the fourth step is carried out at a temperature of from 0° to 10° C. for a period of between 30 and 60 minutes.

* * * * *